United States Patent [19]
Yoneda et al.

[11] Patent Number: 5,942,431
[45] Date of Patent: Aug. 24, 1999

[54] DNA SEQUENCES ENCODING LIPASES AND METHOD FOR PRODUCING LIPASES

[75] Inventors: Tadashi Yoneda; Harumi Takada, both of Chiba; Kei Ohno, Tokyo; Junji Sasuga, Chiba, all of Japan

[73] Assignee: Novo Nordisk A/S, Bagsvaerd, Denmark

[21] Appl. No.: 08/875,062

[22] PCT Filed: Feb. 23, 1996

[86] PCT No.: PCT/JP96/00426

§ 371 Date: Jul. 10, 1997

§ 102(e) Date: Jul. 10, 1997

[87] PCT Pub. No.: WO96/27002

PCT Pub. Date: Sep. 6, 1996

[30] Foreign Application Priority Data

Feb. 27, 1995 [JP] Japan ................................ 7-38527

[51] Int. Cl.⁶ .............. C12N 9/20; C12N 1/20; C12N 15/00; C07H 21/04
[52] U.S. Cl. ................. 435/198; 536/23.2; 536/23.7; 435/69.1; 435/252.3; 435/320.1; 530/350

[58] Field of Search .................... 435/198, 69.1, 435/252.3, 320.1; 536/23.2, 23.7; 530/350

[56] References Cited

U.S. PATENT DOCUMENTS 5,454,971  10/1995  Sakai et al. .
5,766,913   6/1998  Lin et al. ................................ 435/198

FOREIGN PATENT DOCUMENTS 6-153942  6/1994  Japan .
7-67636   3/1995  Japan .

OTHER PUBLICATIONS

Silva et al., GBF Monographs, vol. 16, pp. 416–420.
Sugihara et al., J. Biochem, vol. 112, pp. 598–603 (1992).

*Primary Examiner*—Robert A. Wax
*Assistant Examiner*—Tekchand Saidha
*Attorney, Agent, or Firm*—Steve T. Zelson, Esq; Valeta Gregg, Esq.

[57] ABSTRACT

DNA sequences encoding lipases and method for producing the lipases. The disclosed lipases are industrially useful in, for example, detergents, food processing, paper making, oil manufacturing.

48 Claims, 8 Drawing Sheets

5,942,431

DNA SEQUENCES ENCODING LIPASES AND METHOD FOR PRODUCING LIPASES

CROSS-REFERENCE TO RELATED APPLICATIONS

This application is a 35 U.S.C. 371 national application of PCT/JP96/00426 filed Feb. 23, 1996, the contents of which are fully incorporated herein by reference.

TECHNICAL FIELD

The present invention relates to a novel gene encoding a lipase as a lipid degradation enzyme industrially useful for detergents, food processing, paper making, oil manufacturing or the like and the nucleotide sequence thereof; a gene encoding the protein involved in the production of the lipase and the nucleotide sequence thereof; a recombinant vector carrying these genes, a transformant carrying the recombinant vector; and a method for producing the lipase using the transformant.

BACKGROUND ART

As lipase-producing microorganisms, there have been known genus Pseudomonas, genus Alcaligenes, genus Mucor, genus Candida, genus Humicola, genus Rhizomucor and the like. Genes have been isolated from some of them, and a great number of lipase genes have been isolated from microorganisms of the genus Pseudomonas, in particular. Currently known such lipase genes include those from *Pseudomonas fragi* (Japanese Patent Laid-open Nos. Sho 62-228279 and Hei 2-190188), *Pseudomonas cepacia* (Japanese Patent Laid-open Nos. Hei 3-47079 and Hei 3-87187), *Pseudomonas putida* (EP 268 452), *Pseudomonas pseudoalcaligenes* (Japanese Patent Laid-open No. Hei 3-500845), *Pseudomonas aeruginosa* (EP 334 462), *Pseudomonas glumae* (Appl. Envir. Microbiol. (1992), 3738–3791), and *Pseudomonas fluorescens* (Appl. Envir. Microbiol. (1992) 58, 1776–1779).

It has been known that a protein encoded by a gene region downstream the lipase structural gene is involved in the lipase production in some bacteria of the genus Pseudomonas. For lipase production in *Pseudomonas cepacia*, the gene in the downstream region is essential, irrespective of the species of a host bacterium (EP 331 376). It has been known also that irrespective of the species of a host bacterium, the protein with an effect of stabilizing lipase is encoded by the region in the lipase produced from *Pseudomonas glumae* (EP 464 922).

Alternatively, a homologous host-vector system of *Pseudomonas pseudoalcaligenes* exerts an effect of elevating lipase production, but the gene in the downstream region is not essential for lipase production in a heterologus host-vector system thereof (EP 334 462). Furthermore, the gene in the downstream region is not present in *Pseudomonas fragi*.

It has been known conventionally that the washing effect of a detergent can be elevated when the detergent is blended with a lipase to degrade and remove the lipid attached to articles to be washed. The use is described in H. Andree, et. al., "Lipase as Detergent Components", Journal of Applied Biochemistry, 2, 218–229 (1980) and the like.

Preferably, a lipase to be blended with detergents can satisfactorily exert its lipase activity in a detergent solution. Under routine washing conditions, the pH of washing solutions reside in an alkaline region, so a lipase functioning at an alkaline pH is demanded. Additionally, it has been known that lipid stain is relatively readily removed generally under high temperature and high alkaline conditions but cannot sufficiently be removed through washing at low temperatures (at 60 or less). Not only in Japan where washing has conventionally been carried out at low temperatures, but also in European countries and USA, the washing temperature is likely lowered. Thus, preferably, a lipase to be blended in detergents should satisfactorily function even at low temperatures. Additionally, it is preferable that the lipase to be blended into detergents should sufficiently exhibit its functions during washing even in the presence of detergent components such as surfactant, and protease or bleach contained in many of detergents. Furthermore, preferably, the lipase to be blended into detergents should be stable in the concurrent presence of components contained in the detergents even when the lipase is stored in a blended state in the detergents.

As lipase-producing microorganisms, there have been known the genus Pseudomonas, the genus Alcaligenes, the genus Achromobacter, the genus Mucor, the genus Candida, the genus Humicola, the genus Rhizomucor and the like. Because most of the lipases from these bacterial strains have an optimum pH in a neutral to mild alkaline region, the lipases cannot work sufficiently in alkaline detergent solutions or are poorly stable therein. Still furthermore, the individual lipases from the genus Achromobacter, the genus Mucor, the genus Candida, and the genus Humicola are strongly inhibited of their activities in the presence of anionic surfactants.

Lipase-producing bacteria of the genus Pseudomonas include *Pseudomonas fragi, Pseudomonas cepacia, Pseudomonas pseudoalcaligenes, Pseudomonas aeruginosa,* and *Pseudomonas fluorescens,* but known enzymes having been isolated from these bacterial strains cannot satisfy the properties described above.

DISCLOSURE OF THE INVENTION

The present invention relates to a method for efficiently producing a lipase with excellent properties for use in industrial fields such as detergent industry, particularly lipase S from a strain SD 705 (FERM BP4772).

More specifically, the present invention relates to a gene encoding the lipase S and the nucleotide sequence thereof; a gene encoding a protein involved in the production of the lipase S and the nucleotide sequence thereof; a recombinant vector carrying these genes; a transformant through transformation with such recombinant vector; and a method for producing the lipase S from such transformant.

DETAILED DESCRIPTION OF THE INVENTION

Figure 1:
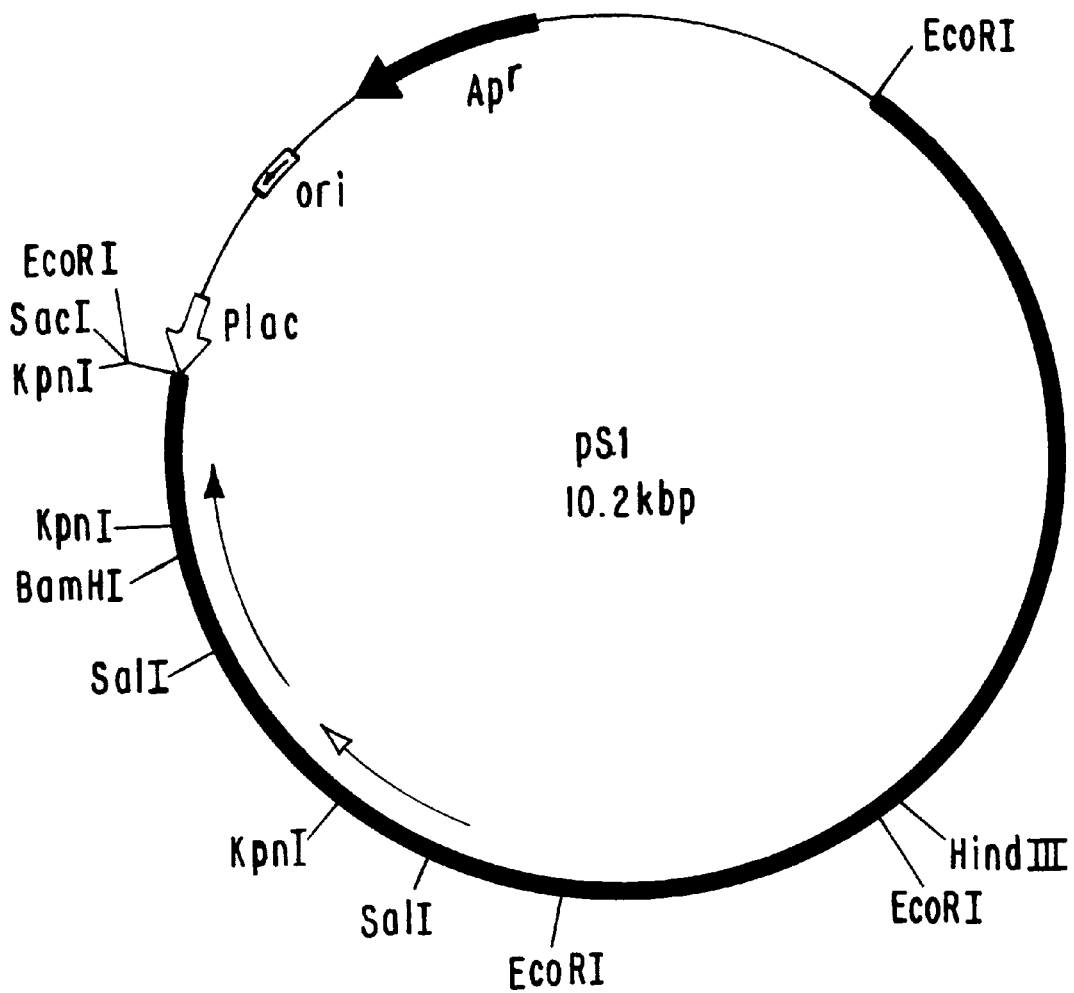
FIG. 1 is a restriction map of plasmid pS1.

From Pseudomonas sp. strain SD 705 (Accession No. FERM BP-4772) firstly deposited by the present inventors at the Life Engineering and Industrial Technology Research Institute, the Agency of Industrial Science and Technology, at 1-3, Higashi 1-chome, Tsukuba-shi, Ibaraki-ken, Japan and then transferred under the Budapest Treaty to international deposition, the present inventors have isolated a DNA fragment carrying the gene encoding the lipase S and the gene encoding the protein involved in the production. The strain SD 705 of the genus Pseudomonas belongs to lipase S-producing bacteria useful for detergent and the like. Introducing the DNA fragment into a host cell and culturing the resultant transformant in a culture medium, it has been confirmed that lipase S was generated in the culture. Thus, the present invention has been achieved.

More specifically, the present invention is to provide what will be described below.

1. A gene encoding the amino acid sequence of Sequence No. 1.
2. A gene carrying the lipase-encoding nucleotide sequence of Sequence No. 2.
3. A gene encoding the amino acid sequence of Sequence No. 3.
4. A gene carrying the nucleotide sequence of Sequence No. 4, which encodes the protein involved in the lipase production.
5. A gene described in any one of 1 to 4, which is derived from bacteria of the genus Pseudomonas.
6. A gene described in any one of 1 to 4, which is derived from Pseudomonas sp. strain SD 705 (Accession No. FERM BP4772).
7. A DNA containing the whole or a part of the nucleotide sequence of the gene described in any one of 1 to 6.
8. A DNA hybridizable with the whole or a part of the nucleotide sequence of the gene described in 3 or 4.
9. A recombinant DNA inserted into a vector replicable in a host microbial cell, so that at least one of the genes described in 1 to 4 might be expressed in the host microbial cell.
10. A recombinant chromosomal DNA generated by incorporating at least one of the genes described in 1 to 4 into a microbial chromosome via homologous recombination.
11. A transformed host microorganism, having been transformed with the recombinant DNA described in 9.
12. A transformed microorganism carrying the recombinant chromosomal DNA described in 10.
13. A transformed microorganism described in 11, wherein the microorganism is a bacterium of the genus Escherichia, Pseudomonas or Bacillus.
14. A transformed microorganism described in 12, wherein the microorganism is a bacterium of the genus Pseudomonas or Bacillus.
15. A transformed microorganism described in 11 or 12, wherein the microorganism is *Pseudomonas alcaligenes, Pseudomonas pseudoalcaligenes, Pseudomonas mendocina,* or *Bacillus subutilis*.
16. A transformed microorganism described in 11 or 12, wherein the microorganism is Pseudomonas sp. strain SD 705 (Accession No. FERM BP4772), *Pseudomonas mendocina* strain SD 702 (Accession No. FERMBP4291), Bacillus strain NKS-21 (Accession NO. FERM BP-93-1) or a variant thereof.
17. A method for producing the lipase, comprising culturing at least one of the transformed host cells described in 11 to 16 to produce a culture containing the lipase and isolating the lipase.

The present invention will now be described hereinbelow in detail.

Isolation of gene

In accordance with the present invention, the lipase-encoding gene can be isolated from chromosomal DNAs by known methods such as colony hybridization and the formation of a clear zone on a plate medium. More specifically, firstly, a chromosome library is prepared. If the whole or a part of the amino acid sequence of the lipase is known, an oligonucleotide probe corresponding to the whole or a part of the sequence is then prepared and using the probe, the gene encoding the lipase can be isolated through colony hybridization.

When the amino acid sequence of the lipase absolutely is not known, an oligonucleotide corresponding to a sequence around the active center residue may be used as the probe, which sequence has generally been known to be highly preserved in lipases from microbial organisms.

Otherwise, using as primers oligonucleotides independently corresponding to two different preserved sequences and as a template a chromosome with an objective lipase gene, the sequence between the two primers is enzymatically synthesized via DNA polymerase, to prepare a double-stranded DNA, of which both the strands may be used as the probes.

Otherwise, a chromosome library is prepared in a bacterium with no lipase production potency, and is then cultured in an agar plate containing a sparingly soluble substrate of lipase. A bacterium containing a chromosomal DNA fragment carrying the lipase gene decomposes the substrate around the colony, so that the screening of the bacterium can be conducted on the basis of the formation of a clear zone. By this method, the gene encoding the lipase may be isolated, but any of these methods may be used satisfactorily.

By colony hybridization using as the probe the whole of the lipase-encoding gene or a part of the 3' region thereof, the gene encoding the protein involved in the lipase production may be isolated as a DNA fragment downstream the lipase gene, from the chromosomal DNA.

Host

Any host capable of expressing the isolated gene may be used as the host to introduce the gene, including for example bacteria of genera Pseudomonas, Escherichia, and Bacillus.

Bacteria of genus Pseudomonas are preferably Pseudomonas sp. strain SD 705 (Accession No. FERM BP4772) or variants thereof, *Pseudomonas alcaligenes, Pseudomonas pseudoalcaligenes* and *Pseudomonas mendocina*. More preferably, the bacteria are Pseudomonas sp. strain SD 705 or variants thereof, *Pseudomonas mendocina* strain SD 702 (Accession No. FERM BP4291) or variants thereof.

As the bacteria of genus Escherichia, preference is given to *Escherichia coli*.

Bacteria of genus Bacillus are preferably *Bacillus subtilis, Bacillus amyloliquefaciens, Bacillus licheniformis, Bacillus firmus, Bacillus lentus,* and *Bacillus alcalophilus*. More preferably, the bacteria belong to Bacillus sp. strain NKS-21 (Accession No. FERM BP-93-1) or variants thereof.

Transformation

The recovered lipase gene and the gene encoding the protein responsible for the production of the lipase are introduced into a host bacterium. These two genes are linked concurrently to one vector so that the same sequence as in the chromosome can be regenerated or the genes are independently linked to two vectors capable of coexisting in a host cell.

In a host except the bacteria of genus Pseudomonas, if used, the genes are inserted and linked between a promoter and signal sequence and a terminator, both functioning in the host, so that the genes can be expressed in the host. Using a recombinant vector with the genes linked therein, a host bacterium is transformed. When the two genes are linked to different vectors, only the vector carrying the lipase gene singly may be used for transformation or the two recombinant vectors are simultaneously used for transformation. In *Escherichia coli* if used as a host, for example, plasmids of pUC or pACYC can be used. In bacteria of genus Bacillus, if used as hosts, plasmids of pUB110 and pE194 can be used.

In bacteria of genus Pseudomonas if used as hosts, plasmids of RSF1010, etc. can be used. The genes can thereby be stably harbored outside the chromosomes of the host bacteria. The genes can also be introduced therein by a method for incorporating a DNA of non-replicable form in a host bacterium into the chromosome.

Generation of lipase

In bacteria of genus Pseudomonas if used as hosts, the lipase is secreted into the culture broth. The separation and purification of the lipase from the culture broth can be carried out by adding ammonium sulfate to the culture broth, fractionating crude lipase, removing the ammonium sulfate through dialysis, and isolating the lipase through a CM cellulose column, to purify the lipase as a single band by SDS polyacrylamide gel electrophoresis. However, the lipase generation and purification are not limited to the methods described above, but as a matter of course other methods are applicable.

Properties of lipase S

The lipase S thus produced by the methods described above has the following properties.

1. Action
   The lipase S acts on triglyceride to hydrolyze its esters.
2. Substrate specificity
   The lipase S hydrolyzes a wide variety of glycerides and esters.
3. Active pH and optimum pH
   When measured in a range of pH 8 to 12 using the pH-stat method on a substrate olive oil, the active pH is 8 to 12 while the optimum pH is about 10.7.
4. Active temperature and optimum temperature
   The active temperature and optimum temperature are 30 to 80° C. and 60±5° C., respectively, when measured using triolein emulsion as the substrate within a range of 30 to 80° C.
5. Effects of detergents
   The lipase S has a higher activity in solutions of various detergents containing protease.

BEST MODE OF CARRYING OUT THE INVENTION

The present invention will now be described with reference to the following examples, but the invention is not limited to these examples.

EXAMPLE 1

Preparation of chromosomal DNA

Supplementing an L medium (1% polypeptone, 0.5% yeast extract, and 0.5% sodium chloride) with 10% sodium carbonate (3 ml) and adjusting the medium to pH 9, inoculating then the Pseudomonas sp. strain SD 705 in the resulting L medium (1000 ml), prior to overnight culturing at 35° C., and centrifuging the resulting medium, the bacteria were recovered. The bacteria were suspended in a 50 mM Tris-HCl buffer, pH 8 (8 ml) containing 0.4 M sodium chloride and 10 mM EDTA. Adding lysozyme and RNase A thereto so as to reach final concentrations of 0.5 mg/ml and 0.05 mg/ml, respectively, followed by gentle shaking at 37° C. for 30 minutes, and further adding sodium dodecyl sulfate (SDS) to the resulting mixture so as to reach a final concentration of 1%, prior to gentle shaking at 37° C. for 30 minutes, the bacteria were lyzed. Subsequently, the bacteria were heated at 60° C. for 10 minutes, for complete solubilization. To the resulting solution was added an equal amount of phenol saturated with TE buffer (1 mM EDTA-containing 10 mM Tris-HCl buffer, pH 8), followed by gentle mixing while the vessel was inversely held with the bottom upward, and after centrifugation, the resulting upper aqueous phase was recovered. The above procedure was repeated three times. To the resulting aqueous phase recovered at the third time was added a 3-fold volume of ethanol cooled at −20° C., to wind and isolate the precipitate around a plastic bar. The precipitate was then rinsed with ethanol, dried under reduced pressure and again solubilized in the TE buffer (1 ml).

EXAMPLE 2

Preparation of chromosomal DNA library

After partially digesting the chromosomal DNA with a restriction endonuclease Sau3AaI, followed by agarose electrophoresis, a 2- to 10-kbp DNA fragment was recovered. Alternatively, a plasmid pUC 118 was digested with BamHI, for subsequent treatment with alkali protease. The two fragments were linked together with T4 DNA ligase. After culturing the resulting linking product in the L medium, the culture was then added to *Escherichia coli* strain JM 101 (0.3 ml) treated with 50 mM calcium chloride, followed by incubation at 0° C. for 30 minutes. To the resulting mixture was added the L medium (to a final volume of 1 ml), followed by shaking at 37° C. for one hour. The resulting culture was coated on an L plate medium containing 50 ppm ampicillin, for overnight culturing at 37° C. Consequently, a tranformant of is about 1,000 colonies was recovered.

EXAMPLE 3

Preparation of oligonucleotide probe

The N-terminal amino acid sequence of the purified lipase was analyzed by a protein sequencer Model 476A (manufactured by Applied Biosystems, Co., Ltd.), to recover consequently the Sequence No. 5. Based on the Sequence, an oligonucleotide probe as shown as Sequence No. 6 was prepared on a DNA synthesizer. This probe was labelled, using ECL (trade name; 3'-oligolabelling and detection system, Amasham life science, Co., Ltd.).

EXAMPLE 4

Isolation of gene encoding lipase

The transformant of about 1,000 colonies was overnight cultured on a nylon filter placed on an L plate medium at 37° C. Peeling off the filter, the bacteria were lyzed for 10 minutes on a filter impregnated with 0.5M sodium hydroxide/1.5 M sodium chloride, which were then neutralized two times on a filter impregnated with 1.5M sodium chloride/1 M Tris-HCl buffer, pH 7 for 7 minutes. After firing the filter at 80° C. for 2 hours, the remaining bacteria were washed in 0.5% SDS/6×SSC (1×SSC means a 150 mM sodium chloride/15 mM sodium citrate solution; n×SSC means a solution at n-fold concentrations of 150 mM sodium chloride/15 mM sodium citrate solution). In a 0.1% SDS/5×SSC/5×Denhardts solution [0.1% phycol, 0.1% polyvinyl pyrrolidone, and 0.1% bovine serum albumin (BSA)], the pre-hybridization on the filter was carried out at 60° C. for one hour. To an identical solution was added the labelled oligonucleotide probe for the hybridization on the filter overnight at 60° C. Subsequently, the filter was washed in 0.1% SDS/1×SSC at 60° C. for 15 minutes and then in 0.1% SDS/0.5×SSC at 60° C. for 15 minutes. This was subjected to detection according to the protocol of ECL (trade name; 3'-oligolabelling and detection system).

Figure 2:
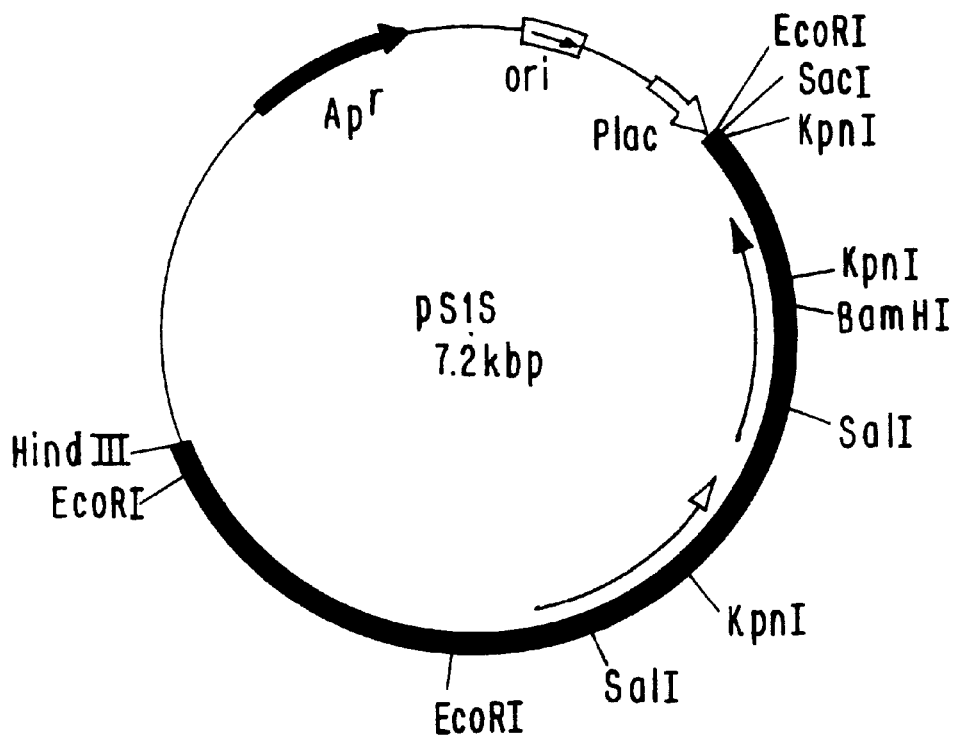
FIG. 2 is a restriction map of plasmid pS1S.
Figure 3:
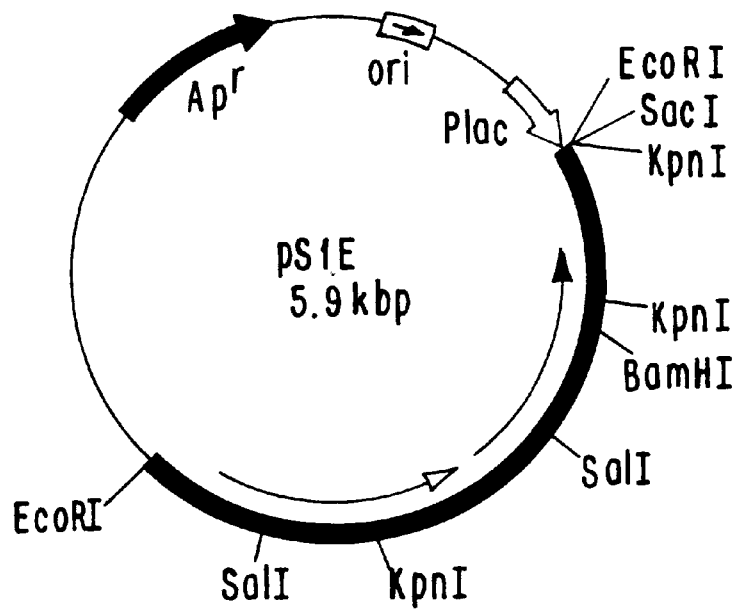
FIG. 3 is a restriction map of plasmid pS1E.

As the consequence of such colony hybridization, a number of positive colonies were recovered. From one of the resulting colonies, a plasmid was recovered, followed by digestion with restriction endonucleases EcoRI and PstI, SacI and XbaI, to prepare fragments. These fragments were separated by agarose electrophoresis to estimate the length of the inserted fragment, which indicates that a DNA fragment of about 7 kbp was recovered. The plasmid pS1 was digested with a variety of restriction endonucleases, to prepare a restriction map. Further, the plasmid was separated by agarose gel electrophoresis and adsorbed on a nylon filter. By the same procedures as for colony hybridization, southern hybridization was carried out. Finally, the plasmid was hybridized with a HindIII -SacI fragment of about 4 kbp and an EcoRI fragment of about 2.7 kbp. Consequently, it was assumed that the gene encoding lipase S and the gene encoding the protein involved in the production thereof was estimated to be carried in the HindIII -SacI fragment of about 4 kbp and the EcoRI fragment of about 2.7 kbp, respectively. FIG. 1 shows the restriction map of pS1. Herein, the white arrow depicts the lipase gene; the black arrow depicts the gene responsible for the lipase production; "Plac" represents lac promoter; "ori" represents replication initiating point; and "Ap'" represents ampicillin-resistant gene. Recovering these fragments and individually linking the fragments to the HindIII-SacI site or EcoRI site of the plasmid pUC118 (manufactured by TaKaRa Brewery, K.K.), thereby transforming the Escherichia coli strain JM 101, plasmids pS1S and pS1E individually containing the respective DNA fragments were recovered. FIGS. 2 and 3 depict the restriction maps of pS1S and pS1E, respectively (the symbols in the figures are the same as in FIG. 1).

EXAMPLE 5
Determination of the nucleotide sequence of lipase gene

Using the plasmid pS1E, the nucleotide sequences of the gene encoding the lipase S and the gene encoding the protein involved in the production of the lipase S were determined according to the dideoxy method by Sanger (Sanger, F., Nicklen, S., Coulson, A. R. (1977), Proc. Natl. Acad. Sci. USA., 74, 5463). More specifically, the nucleotide sequencing was carried out on a DNA sequencer (Model 370A; Applied Biosystems, Co., Ltd.) using a dideoxy terminator sequencing kit (Applied Biosystems, Co. Ltd.). Consequently, the lipase-encoding nucleotide sequence of the Sequence No. 2 and the nucleotide sequence encoding the protein involved in the production of the lipase, as shown as Sequence No. 4, were recovered. The putative amino acid sequences based on these sequences are shown as Sequence Nos. 1 and 3.

EXAMPLE 6
Construction of recombinant vector and preparation of transformant i) *Escherichia coli*

Figure 4:
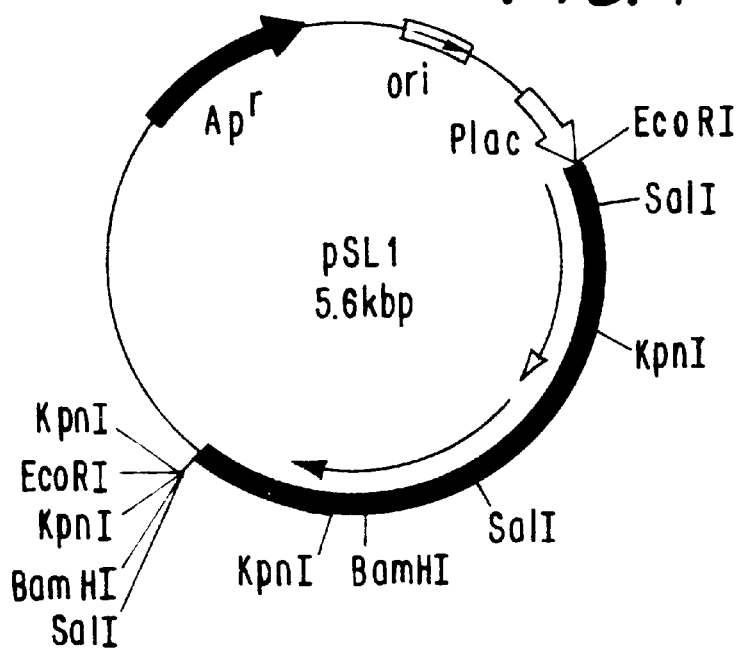
FIG. 4 is a restriction map of plasmid pSL1.

An oligonucleotide of Sequence No. 7 was chemically synthesized, which worked to add the EcoRI site to the 5' terminus of a sequence corresponding to a segment containing the ribosome linking site (SD sequence) and the initiation codon of the lipase gene. Mixing two oligonucleotides, namely the oligonucleotide and commercially available M13 primer RV (manufactured by TaKaRa Brewery K.K.), with the plasmid pS1E for polymerase chain reaction (POLYMERASE CHAIN REACTION (PCR)), a DNA fragment carrying the lipase gene including the SD sequence and the gene encoding the protein involved in the production thereof was generated. After completely digesting the fragment with EcoRI and fractionating the digested products by agarose gel electrophoresis, the products were extracted and purified from the agarose gel. After completely digesting the plasmid pUC118 with EcoRI and mixing the resulting digested products with the DNA fragment thus purified for linking them together with T4 DNA ligase for transforming the *Escherichia coli* strain JM 101, ampicillin-resistant transformants were isolated. From these transformants, the plasmid DNA was extracted, purified and analyzed, so as to confirm that the transformants thus produced carried a plasmid on which the DNA fragment carrying the lipase gene and the gene encoding the protein involved in the production thereof was harbored and inserted into the EcoRI restriction site of pUC118, to express the lipase gene and the gene encoding the protein involved in the production thereof downstream the lac promoter. The plasmid is defined as pSL1. FIG. 4 shows the restriction map of pSL1 (the symbols in the figure are the same as in FIG. 1).

Figure 5:
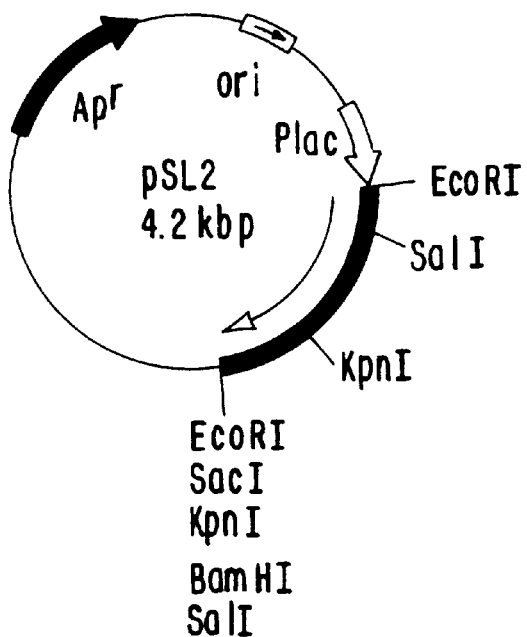
FIG. 5 is a restriction map of plasmid pSL2.

An oligonucleotide to add the EcoRI site to the 3' terminus of the lipase gene, as shown as Sequence No. 8, was chemically synthesized. Mixing the oligonucleotide and the oligonucleotide preliminarily synthesized, as shown as Sequence No. 7, with the plasmid pS1E for polymerase chain reaction (PCR), a DNA fragment containing only the lipase gene including the SD sequence was recovered. The fragment was completely digested with EcoRI, and was then linked with the plasmid pUC118 in the same manner as described above for transformation, to recover a transformant carrying a plasmid pSL2 on which the DNA fragment containing only the lipase gene was harbored and inserted into the EcoRI restriction site of pUC118 to express the lipase gene downstream the lac promoter. FIG. 5 shows the restriction map of the pSL2 (the symbols in the figure are the same as in FIG. 1).

ii) Pseudomonas

Figure 6:
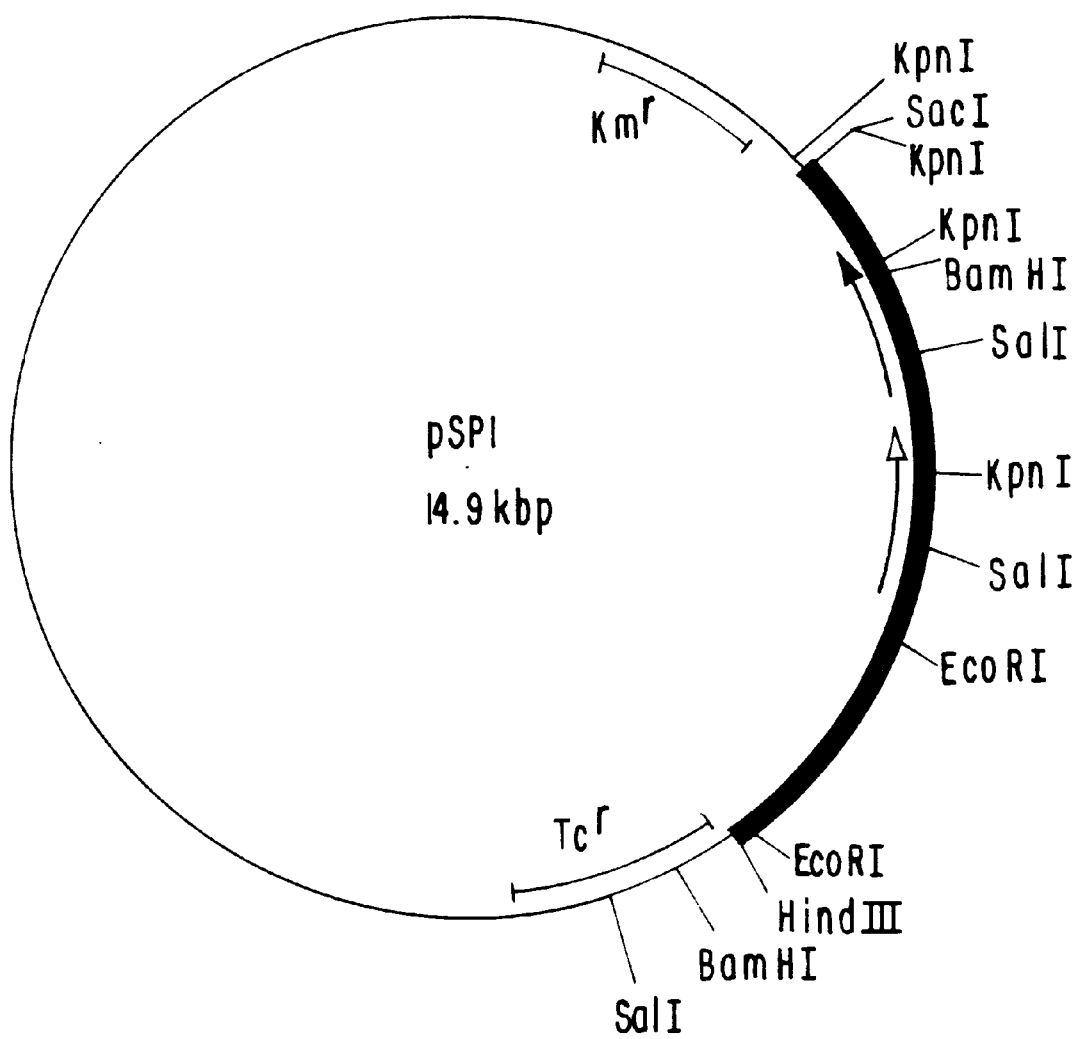
FIG. 6 is a restriction map of plasmid pSP1.

After completely digesting the plasmid pS1S with HindIII and SacI, a DNA fragment containing the lipase gene and the gene encoding the protein involved in the production thereof was fractionated by agarose gel electrophoresis followed by extraction and purification from the agarose gel. After completely digesting the plasmid pMFY42 with the HindIII and SacI, the resulting products were mixed with the DNA fragment thus purified, followed by linking with T4 DNA ligase to transform *Escherichia coli* strain JM 101 to select kanamycin-resistant colonies. From these transformants, the plasmid DNA was extracted, purified and analyzed, to recover a plasmid pSP1 in which a DNA fragment carrying the lipase gene and the gene encoding the protein involved in the production thereof was inserted in between the HindIII- and SacI digestion sites of pMFY 42. FIG. 6 shows the restriction map of pSP1. Herein, the white arrow and black arrow represent the same as in FIG. 1. "Km'" represents kanamycin-resistant gene; and "Tc'" represents tetracycline-resistant gene.

Figure 7:
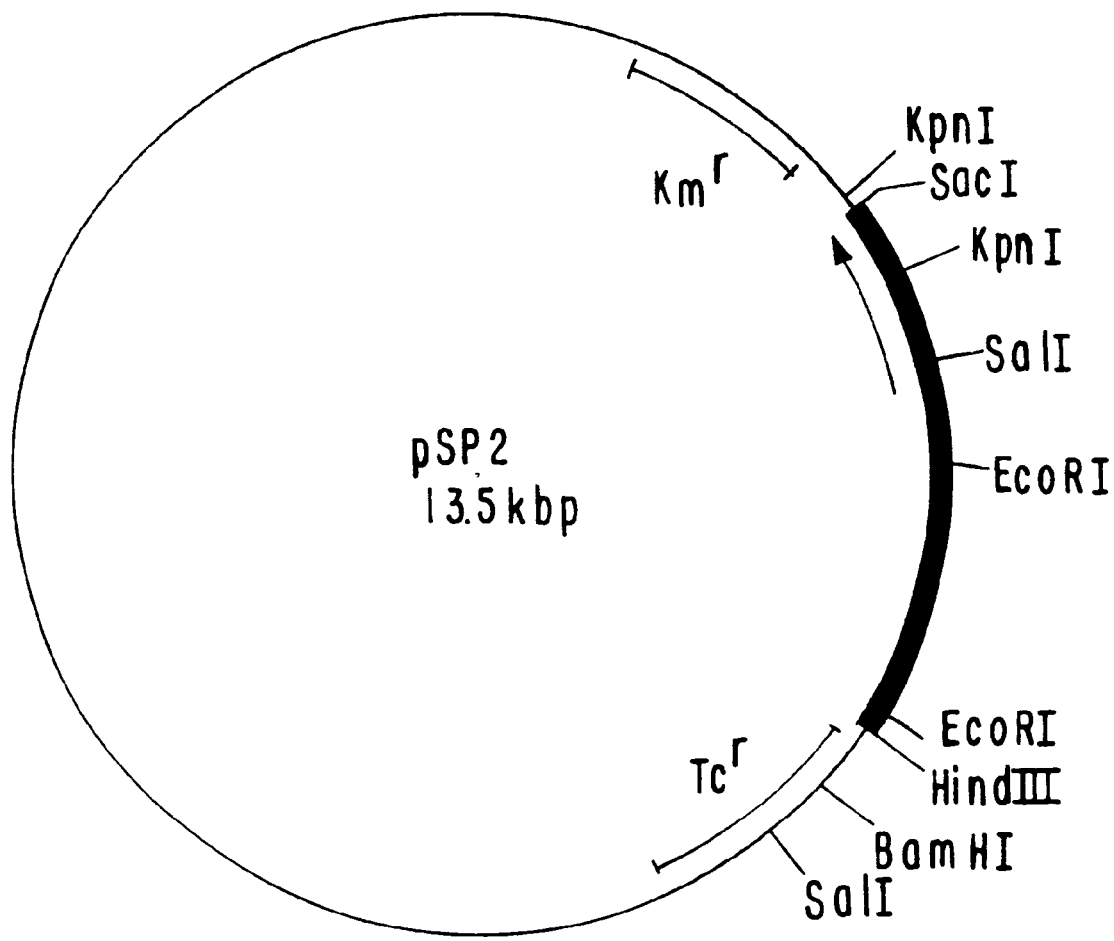
FIG. 7 is a restriction map of plasmid pSP2.

Two oligonucleotides, namely a commercially available M13 primer M4 (manufactured by TaKaRa Brewery, K. K.) and the oligonucleotide as shown as Sequence No. 9, were mixed with the plasmid pS1S for polymerase chain reaction (PCR), to recover a DNA fragment containing only the lipase gene. The fragment was completely digested with the HindIII and SacI, and the resulting digested products were then linked to the plasmid pMFY42 in the same manner as described above, to recover a DNA fragment containing only the lipase gene in between the HindIII- and SacI digestion sites of pMFY 42. FIG. 7 shows the restriction map of pSP2 (the symbols in the figure are the same as in FIG. 6).

By electrophoresis, Pseudomonas sp. strain SD 705 (Accession No. FERM BP-4772) was transformed using the plasmids pSP1 and pSP2, to select kanamycin-resistant colonies. More specifically, firstly, the strain SD705 was grown in an L liquid medium (5 ml) adjusted to pH 9, until the OD reached 0.5. The bacteria were recovered by centrifugation. The bacteria were suspended in sterilized water, which were then again recovered and resuspend in sterilized water (0.5 ml). Adding the plasmid DNA to the bacterial suspension, which was then transferred into a cell with electrodes, a high-voltage electric pulse was applied to the DNA. Subsequently adding the L liquid medium (1 ml), pH 9 into the bacterial suspension, followed by shaking culture at 37° C. for one hour, the resulting suspension was coated on an L plate medium, pH 9 containing 50 ppm kanamycin and olive oil emulsion as a lipase substrate. After overnight culturing at 35° C., grown colonies with clear zones formed around themselves were selected to recover a transformed strain.

Strain LD 9 as a lipase depletion strain of Pseudomonas mendocina strain SD 702 (Accession No. FERM BP4291) was transformed to generate a transformant. By making N-methyl-N'-nitro-N-nitrosoguanidine act on Pseudomonas mendocina strain SD 702, which was then inoculated on a plate medium containing the lipase substrate to select a strain without any clear zone formed, herein, the strain LD 9 was recovered.

iii) Bacillus

An oligonucleotide capable of adding the XbaI site to the N-terminus of mature lipase, as shown as Sequence No. 10, was chemically synthesized. Additionally, an oligonucleotide capable of adding the XbaI site to the 3'-terminus of the gene encoding the protein involved in the production of the lipase, as shown as Sequence No. 11, was chemically synthesized. Mixing these two oligonucleotides with a plasmid pS1E for polymerase chain reaction (PCR), a DNA fragment carrying the mature lipase gene and the gene encoding the protein involved in the production thereof was recovered. After completely digesting the fragment with XbaI and linking the digested fragments with plasmid pUC118, a plasmid pSM1 was recovered, on which a DNA fragment carrying the mature lipase gene and the gene encoding the protein involved in the production thereof was harbored and inserted in the XbaI digested site of pUC118.

An oligonucleotide capable of adding the XbaI site to the C-terminus of the lipase, as shown as Sequence No. 12, was chemically synthesized. Mixing the oligonucleotide and the oligonucleotide as shown as Sequence No. 10 with the plasmid pS1E for polymerase chain reaction (PCR), a DNA fragment carrying only the mature lipase gene was recovered. After completely digesting the fragment with XbaI and linking the digested fragments with the plasmid pUC 118 in the same manner as described above, a plasmid pSM2 was recovered, on which a DNA fragment carrying the mature lipase gene and the gene encoding the protein involved in the production thereof was harbored and inserted in the XbaI digested site of pUC118.

Oligonucleotides as shown as Sequence Nos. 13 and 14 were chemically synthesized. Mixing these two oligonucleotides with plasmid pSDT812 (Japanese Patent Laid-open No. Hei 1-141596) for polymerase chain reaction (PCR), a DNA fragment including the promoter region of alkali protease and a part of the prepro sequence thereof was recovered. After completely digesting the fragment with EcoRI and XbaI and linking the digested fragments with plasmid pUC118, a plasmid pAP1 was recovered, on which the DNA fragment including the promoter region of alkali protease and a part of the prepro sequence thereof was harbored and inserted in between the EcoRI digestion site and the XbaI digestion site of pUC118.

Oligonucleotides as shown as Sequence Nos. 15 and 16 were chemically synthesized. Mixing these oligonucleotides with the plasmid pSDT812 for polymerase chain reaction (PCR), a DNA fragment including the terminator region of alkali protease was recovered. After completely digesting the fragment with XbaI and HindIII and linking the digested fragments with a plasmid pUC 118 in the same manner as described above, a plasmid pAP2 was recovered, on which a DNA fragment including the terminator region of alkali protease was harbored and inserted in between the XbaI digested site and HindIII digested site of pUC118.

Figure 8:
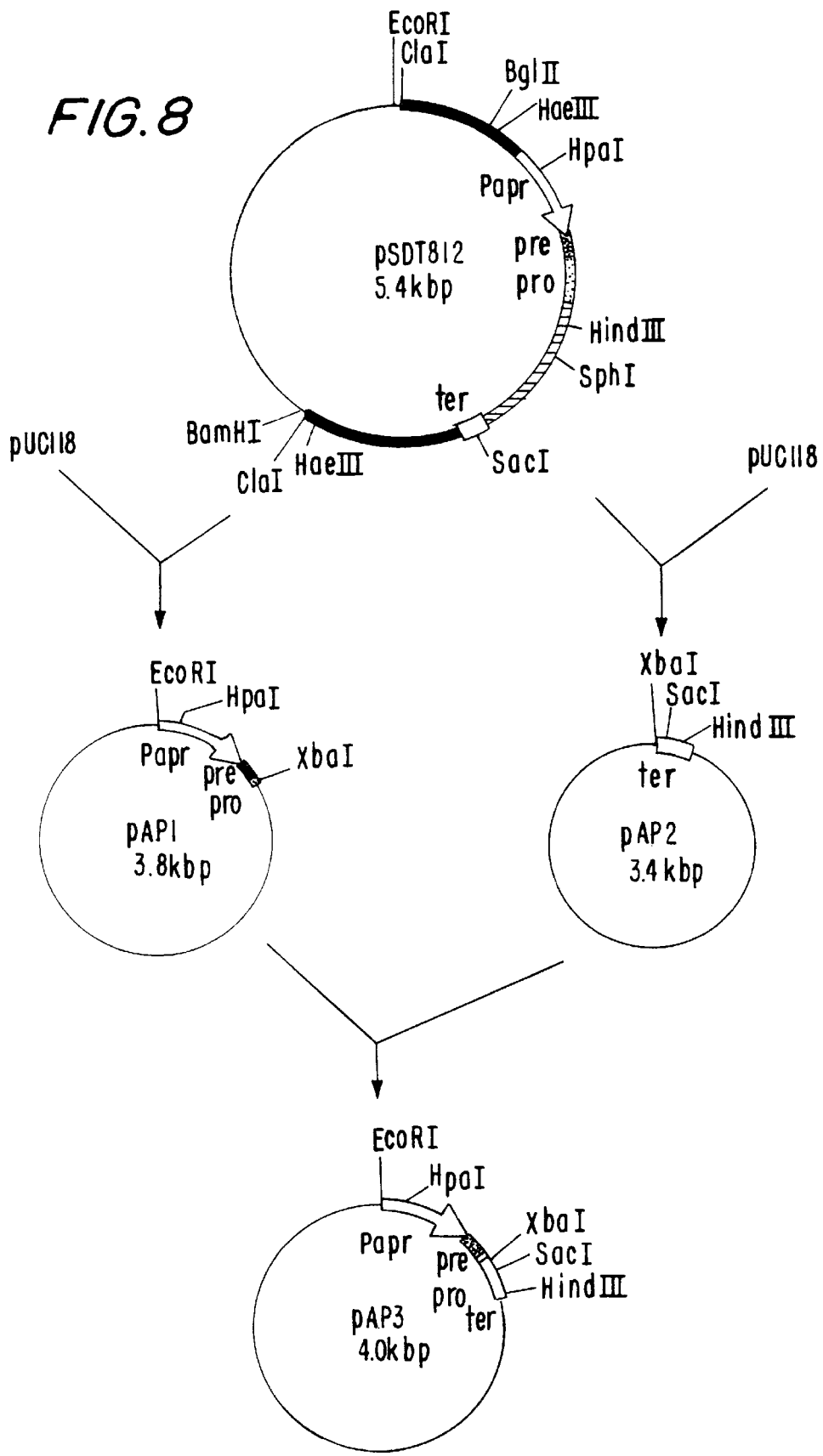
FIG. 8 depicts the constructions of plasmids pAP1, pAP2 and pAP3.

Digesting the plasmid pAP1 with EcoRI and XbaI, a DNA fragment including the promoter region of alkali protease and a part of the prepro sequence thereof was recovered. Additionally, digesting the plasmid pAP2 with XbaI and HindIII, a DNA fragment including the terminator region of alkali protease was recovered. Linking then these two fragments to the plasmid pUC118, a plasmid pAP3 was recovered, on which a DNA fragment including the promoter region, a part of the prepro sequence and the terminator region of alkali protease was harbored and inserted in between the EcoRI digested site and the HindIII digested site of pUC118. FIG. 8 shows the processes of the construction of pAP1, pAP2 and pAP3. Herein, "Papr" represents alkali protease gene promoter; "pre" represents alkali protease pre-sequence; "pro" represents alkali protease pro-sequence; and "ter" represents alkali protease gene terminator.

Digesting plasmids pSM1 and pSM2 with XbaI, two DNA fragments carrying the lipase gene were recovered. Linking these two fragments independently to the XbaI site of the plasmid pAP3, plasmids pAP4 and pAP5 were recovered.

Figure 9:
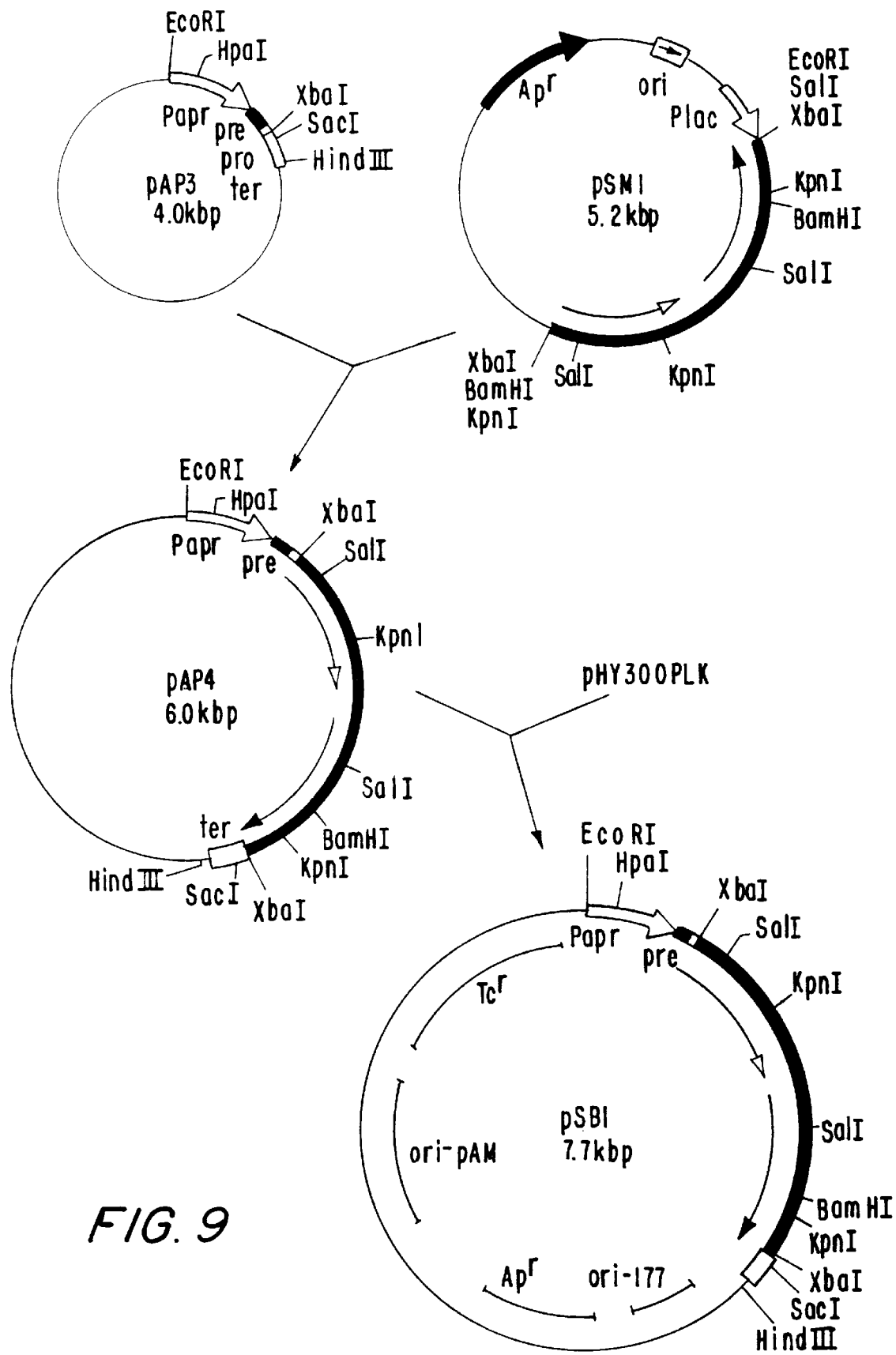
FIG. 9 depicts the construction of plasmid pSB1.
Figure 10:
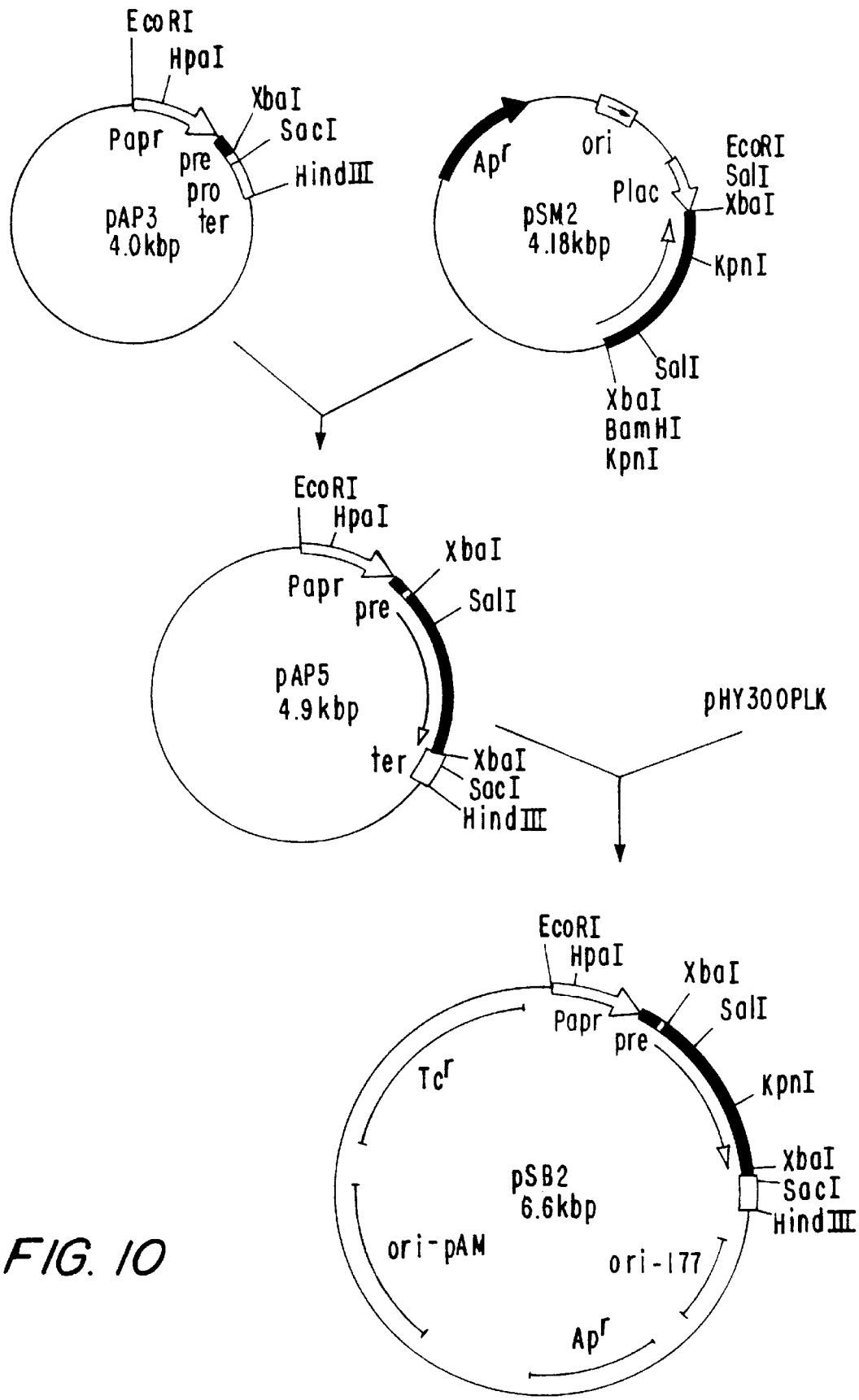
FIG. 10 depicts the construction of plasmid pSB2.

Digesting the plasmids pAP4 and pAP5 with EcoRI and HindIII, two DNA fragments carrying the lipase gene were recovered. Linking these two fragments independently to plasmid pHY300PLK (manufactured by TaKaRa Brewery, K.K.), Bacillus subtilis strain SD-800 (the strain with lower protease production potency, produced by the method described in Japanese Patent Laid-open No. Hei 1-141596) was transformed by the protoplast method. Selecting tetracycline-resistant tranformant strains forming a larger clear zone on an agar medium containing 0.5% olive oil emulsion, the plasmid DNA was extracted and purified from these transformants, to recover plasmids pSB1 and pSB2, on which DNA fragments with the promoter region of alkali protease, a part of the prepro sequence thereof, the mature lipase gene or the mature lipase gene along with the gene encoding the protein involved in the production thereof, and the terminator region of alkali protease were harbored and inserted in between the EcoRI digestion site and the HindIII digestion site of pHY300PLK. FIGS. 9 and 10 depict the processes of the construction of pSB1 and pSB2, respectively (the symbols in the figure are the same as in FIGS. 1, 6 and 8).

Transforming a protease depletion strain of the Bacillus strain NKS-21 (Accession No. FERM BP-93-1) with the plasmids by the protoplast method, a tetracycline-resistant transformed strain was selected. The protease depletion strain of the Bacillus strain NKS-21 was generated, by helping N-methyl-N'-nitro-N-nitrosoguanidine act on the Bacillus strain NKS-21 and inoculating and culturing the resulting strains on a plate medium containing skimmed milk, and thereafter selecting a strain with no formation of any clear zone.

EXAMPLE 7

Preparation of lipase i) *Escherichia coli*

Culturing independently transformed strains carrying plasmids pSL1 and pSL2 in an L liquid medium (5 ml) containing 50 ppm ampicillin under shaking overnight at 37° C. and inoculating 1% of the transformed strains after shaking culture at 37° C. for 3 hours onto the same medium (300 ml), isopropyl-beta-thiogalactopyranoside (IPTG) was added therein to a final concentration of 1 mM, to induce the expression of the lac promoter, followed by another 4-hour shaking culture. Centrifuging the culture and collecting the supernatant, a lipase solution was prepared.

ii) Pseudomonas

Culturing transformed strains carrying the plasmids pSP1 and pSP2 under shaking, in a lipase generation medium (300 ml) containing 1% Tween 80 and having been adjusted to pH 9, at 35° C. for 14 hours, lipase was generated and secreted in the medium. Centrifuging the culture and collecting the supernatant, a lipase solution was prepared.

After fractionating the solution with ammonium sulfate and removing the ammonium sulfate through dialysis and thereafter treating the resulting solution with a CM cellulose column, the solution was purified as a single band by SDS polyacrylamide electrophoresis.

iii) Bacillus

Culturing transformed strains containing the plasmids pSB1 and pSB2 under shaking in a medium (300 ml) containing 1% casein, 1% meat extract and 1% polypeptone and having been adjusted to pH 7.5 with sodium carbonate at 35° C. for 66 hours, lipase was generated and secreted in the medium. Centrifuging the culture and collecting the supernatant, a lipase solution was prepared.

EXAMPLE 8

Activity of lipase

The activity of the lipase solutions from the cultures of *Escherichia coli* and Pseudomonas was determined. The assay of the activity was carried out by a method using as the substrate triolein-polyvinyl alcohol (PVA). More specifically, the following method was used.

A mixture solution of 100 mM ε-aminocaproic acid, 100 mM bis-tris[bis(2-hydroxyethyl)iminotris(hydroxymethyl) methane] and 100 mM TAPS [N-tris(hydroxymethyl) methyl-3-aminopropane sulfonic acid], further containing a lipase solution (0.1 ml) and 1 mM calcium chloride, was pH adjusted with sodium hydroxide, and the resulting solution was defined as buffer solution (pH 8.0; 0.4 ml). Heating then a mixture solution of the buffer solution and triolein emulsion (0.5 ml) in a stoppered test tube at 37° C. for 10 minutes, the reaction was terminated by using 1 N hydrochloric acid (0.2 ml) as the reaction termination solution. Triolein was added into 10 ml of an aqueous 2% polyvinyl alcohol (PVA) solution (10 ml) [Poval PVA 117 (manufactured by KURARAY): Poval PVA 205 (manufactured by KURARAY)=9:1] followed by homogenization, to use herein the resulting mixture as the triolein emulsion. After termination of the reaction, n-hexane (2 ml), isopropyl alcohol (2 ml) and distilled water (1 ml) were added to the reaction mixture under vigorous agitation, and then, the mixture was left to stand. The resulting hexane layer was sampled to assay oleic acid by the TLC-FID method [Minagawa, et. al., Lipids, 18, 732 (1983)]. One unit (1 U) of the activity unit was defined as the enzyme amount generating 1 μmol of oleic acid per one minute.

The activity of each of the lipase solutions (culture supernatant) from the individual transformants is represented as the relative value to the activity of the strain SD 705, which is defined as 100. The activity is shown in Table 1. All the transformants introduced with the lipase gene, expressed the lipase activity under observation; and further, the transformants carrying the plasmids inserted with the DNA fragments including the gene encoding the protein involved in the lipase production, showed higher expression levels of lipase activity than the levels in the transformants carrying only the lipase gene, which indicates that the gene is responsible for the elevation of the lipase production.

TABLE 1

| Plasmid/bacterial strain | Lipase Activity Activity |
|---|---|
| None/JM 101 | 0 |
| pUC118/JM101 | 0 |
| pSL1/JM101 | 20 |
| PSL2/JM101 | 10 |
| None/SD705 | 100 |
| pMFY42/SD705 | 100 |
| pSP1/SD705 | 520 |
| pSD2/SD705 | 320 |
| None/LD9 | 0 |
| pMFY42/LD9 | 0 |
| pSP1/LD9 | 110 |
| pSP2/LD9 | 50 |

EXAMPLE 9

Lipase activity

The activity of lipase from the Bacillus culture was assayed. The activity was assayed by the following procedures according to the method using as the substrate p-nitrophenyl palmitate (pNPP)

pNPP was solubilized in isopropyl alcohol to 2 mg/ml. Mixing the pNPP solution and 100 mM Bicine buffer, pH 8.0 at a ratio of 1:10, the resulting solution was used as a substrate solution. Adding the lipase solution (0.02 ml) into the substrate solution (0.5 ml), and reacting them together at room temperature for 1 to 10 minutes, 1N HCl (0.2 ml) was added to the reaction mixture for termination of the reaction. Then, the absorbance at 405 nm was measured by a spectrophotometer. One pNPP unit (1 pU) of the enzyme was defined as the enzyme amount increasing the absorbance at 405 nm by one per one minute.

The activities of the lipases from the individual transformants are shown in Table2.

TABLE 2

| Plasmid/bacterial strain | Lipase activity Activity |
|---|---|
| None/SD-800 | 0 |
| pHY300PLK/SD-800 | 0 |
| pSB1/SD-800 | 3.2 |
| pSB2/SD-800 | 1.1 |
| None/NKS-21 | 0 |
| pHY300PLK/NKS-21 | 0 |

TABLE 2-continued

Lipase activity

| Plasmid/bacterial strain | Activity |
|---|---|
| pSB1/NKS-21 | 5.2 |
| pSB2/NKS-21 | 2.3 |

Industrial Applicability

In accordance with the lipase gene of the present invention, the generation and modification of lipase S as a lipid degradation enzyme industrially useful in detergents, paper making, oil manufacturing and the like, are readily carried out. Also, in accordance with the gene encoding the protein involved in the lipase production, in accordance with the present invention, the production of lipase S can be elevated, economically advantageously for providing the industrially useful lipase.

Information of deposited microorganisms

The depository of the microorganisms described in the specification and the claims is described hereinbelow, together with the address and deposition date.

1. Pseudomonas sp. strain SD 705 (Accession No. FERM BP-4772)

Depository: The Life Engineering and Industrial Technology Research Institute, the Agency of Industrial Science and Technology, the Ministry of Industry and Trade Address: 1-3, Higashi 1-chome, Tsukuba-shi, Ibaraki-ken, Japan The strain was deposited as P-13781 on Aug. 4, 1993; under the Budapest Treaty, the strain was transferred and internationally deposited as Pseudomonas sp. strain SD 705 (Accession No. FERM BP4772) on Aug. 5, 1994.

2. Pseudomonas alcaligenes strain SD 702 (Accession No. FERM BP4291)

Depository: The Life Engineering and Industrial Technology Research Institute, the Agency of Industrial Science and Technology, the Ministry of Industry and Trade Address: 1-3, Higashi 1-chome, Tsukuba-shi, Ibaraki-ken, Japan The strain was deposited as P-12944 on May 1, 1992; under the Budapest Treaty, the strain was transferred and internationally deposited as Pseudomonas sp. strain SD 702 (Accession No. FERM BP4291) on May 12, 1993.

3. Bacillus strain NKS-21 (Accession No. FERM BP-93-1)

Depository: The Microbial Industrial Technology Research Institute, the Agency of Industrial Science and Technology, the Ministry of Industry and Trade Address: 1-3, Higashi 1-chome, Yatabe-cho, Tsukuba-gun, Ibaraki-ken, Japan As the re-deposition of the FERM BP-93, the strain was re-deposited internationally as FERM BP-93-1 on May 21, 1985.

The depository described in the above item 3 has been reorganized currently as "Life Engineering and Industrial Technology Research Institute, the Agency of Industrial Science and Technology, the Ministry of Industry and Trade", and the address is modified as 1-3, Higashi 1-chome, Tsukuba-shi, Ibaraki-ken, Japan.

We claim:

1. An isolated DNA sequence encoding the amino acid sequence of SEQ ID NO: 1.

2. An isolated DNA sequence comprising the lipase-encoding nucleotide sequence of SEQ ID NO. 2.

3. An isolated DNA sequence encoding the amino acid sequence of SEQ ID NO: 3.

4. An isolated nucleotide sequence encoding the protein of SEQ ID NO: 4.

5. The isolated DNA sequence of claim 1 from bacteria of genus Pseudomonas.

6. The isolated DNA sequence of claim 5, wherein the Pseudomonas strain is SD 705 (FERM BP-4772).

7. The DNA sequence of claim 1, or fragment thereof encoding an enzymatically active lipase.

8. A DNA sequence which hybridizes to the DNA sequence of claim 3 under the following conditions: prehybridization in a 0.1% SDS/5×SSC/5×Denhardts solution at 60° C. for one hour; hybridization overnight at 60° C. followed by washing in 0.1% SDS/1×SSC at 60° C. for 15 minutes and 0.1% SDS/0.5×SSC at 60° C. for 15 minutes.

9. A recombinant DNA generated by incorporating the DNA sequence of claim 1 into a replicable vector in a host microbial cell for the expression of the genes.

10. A recombinant chromosomal DNA generated by incorporation of the sequence of claim 1 into a microbial chromosome by homologous recombination.

11. A transformed host microorganism transformed with the recombinant DNA sequence of claim 9.

12. A transformed microorganism comprising the recombinant chromosomal DNA sequence of claim 10.

13. The transformed microorganism of claim 11, wherein the microorganism is a bacterium of a genus selected from the group consisting of Escherichia, Pseudomonas, or Bacillus.

14. The transformed microorganism of claim 12, wherein the microorganism is a bacterium of the genus Pseudomonas or Bacillus.

15. The transformed microorganism of claim 11, wherein the microorganism is *Pseudomonas alcaligenes, Pseudomonas pseudoalcaligenes, Pseudomonas mendocina*, or *Bacillus subutilus*.

16. The transformed microorganism of claim 11, wherein the microorganism is Pseudomonas sp. strain SD 705, *Pseudomonas alcaligenes* strain SD 702, Bacillus strain NKS-21 or a variant thereof.

17. A method for producing a lipase, comprising culturing the transformed microorganism of claim 11 to produce a culture containing a lipase and isolating the lipase.

18. The isolated DNA sequence of claim 2 from bacteria of genus Pseudomonas.

19. The isolated DNA sequence of claim 18, wherein the Pseudomonas strain is SD 705 (FERM BP4772).

20. A DNA sequence or fragment thereof encoding an enzymatically active lipase according to claim 2.

21. A recombinant DNA generated by incorporating the DNA sequence of claim 2 into a replicable vector in a host microbial cell for the expression of the DNA sequences.

22. A recombinant chromosomal DNA sequence generated by incorporation of the DNA sequence of claim 2 into a microbial chromosome by homologous recombination.

23. A transformed host microorganism comprising the recombinant DNA of to claim 21.

24. The transformed microorganism of claim 23, wherein the microorganism is a bacterium of a genus selected from the group consisting of Escherichia, Pseudomonas, or Bacillus.

25. The transformed microorganism of claim 24, wherein the microorganism is *Pseudomonas alcaligenes, Pseudomonas pseudoalcaligenes, Pseudomonas mendocina*, or *Bacillus subutilus*.

26. The transformed microorganism of claim 25, wherein the microorganism is Pseudomonas sp. strain SD 705, *Pseudomonas alcaligenes* strain SD 702, Bacillus strain NKS-21 or a variant thereof.

27. A method for producing a lipase, comprising culturing the transformed microorganism of claim 23 to produce a culture containing a lipase and isolating the lipase.

28. The isolated DNA sequence of claim 3 from bacteria of genus Pseudomonas.

29. The isolated DNA sequence of claim 28, wherein the Pseudomonas strain is SD 705 (FERM BP-4772).

30. A DNA sequence or fragment thereof encoding an enzymatically active lipase according to claim 3.

31. A recombinant DNA generated by incorporating the DNA sequence of claim 3 into a replicable vector in a host microbial cell for the expression of the DNA sequences.

32. A recombinant chromosomal DNA sequence generated by incorporation of the DNA sequence of claim 3 into a microbial chromosome by homologous recombination.

33. A transformed host microorganism comprising the recombinant DNA of to claim 31.

34. The transformed microorganism of claim 33, wherein the microorganism is a bacterium of a genus selected from the group consisting of Escherichia, Pseudomonas, or Bacillus.

35. The transformed microorganism of claim 34, wherein the microorganism is *Pseudomonas alcaligenes, Pseudomonas pseudoalcaligenes, Pseudomonas mendocina*, or *Bacillus subutilus*.

36. The transformed microorganism of claim 35, wherein the microorganism is Pseudomonas sp. strain SD 705, *Pseudomonas alcaligenes* strain SD 702, Bacillus strain NKS-21 or a variant thereof.

37. A method for producing a lipase, comprising culturing the transformed microorganism of claim 33 to produce a culture containing a lipase and isolating the lipase.

38. The isolated DNA sequence of claim 4 from bacteria of genus Pseudomonas.

39. The isolated DNA sequence of claim 38, wherein the Pseudomonas strain is SD 705 (FERM BP4772).

40. A DNA sequence or fragment thereof encoding an enzymatically active lipase according to claim 4.

41. A DNA sequence which hybridizes to the DNA sequence of claim 4 under the following conditions: prehybridization in a 0.1% SDS/5×SSC/5×Denhardts solution at 60° C. for one hour; hybridization overnight at 60° C. followed by washing in 0.1% SDS/1×SSC at 60° C. for 15 minutes and 0.1% SDS/0.5×SSC at 60° C. for 15 minutes.

42. A recombinant DNA generated by incorporating the DNA sequence of claim 4 into a replicable vector in a host microbial cell for the expression of the DNA sequences.

43. A recombinant chromosomal DNA sequence generated by incorporation of the DNA sequence of claim 4 into a microbial chromosome by homologous recombination.

44. A transformed host microorganism comprising the recombinant DNA of to claim 42.

45. The transformed microorganism of claim 44, wherein the microorganism is a bacterium of a genus selected from the group consisting of Escherichia, Pseudomonas, or Bacillus.

46. The transformed microorganism of claim 45, wherein the microorganism is *Pseudomonas alcaligenes, Pseudomonas pseudoalcaligenes, Pseudomonas mendocina*, or *Bacillus subutilus*.

47. The transformed microorganism of claim 46, wherein the microorganism is Pseudomonas p. strain SD 705, *Pseudomonas alcaligenes* a SD 702, Bacillus strain NKS-21 or a variant thereof.

48. A method for producing a lipase, comprising culturing the transformed microorganism of claim 44 to produce a culture containing a lipase and isolating the lipase.

* * * * *

UNITED STATES PATENT AND TRADEMARK OFFICE
CERTIFICATE OF CORRECTION

PATENT NO. : 5,942,431
DATED : August 24, 1999
INVENTOR(S) : Yoneda et al

It is certified that error appears in the above-identified patent and that said Letters Patent is hereby corrected as shown below:

Col. 23, line 45, claim 19 change "(FERM BP4772)" to --(FERM BP-4772)--

Col. 24, line 35, claim 39 change "(FERM BP4772)" to --(FERM BP-4772)--

Signed and Sealed this

Thirtieth Day of January, 2001

Attest:

Q. TODD DICKINSON

*Attesting Officer*    *Director of Patents and Trademarks*

SEQUENCE LISTING

<160> NUMBER OF SEQ ID NOS: 16

<210> SEQ ID NO 1
<211> LENGTH: 288
<212> TYPE: PRT
<213> ORGANISM: Pseudomonas sp.

<400> SEQUENCE: 1

```
Phe Gly Ser Ser Asn Tyr Thr Lys Thr Gln Tyr Pro Ile Val Leu Thr
 1               5                  10                  15

His Gly Met Leu Gly Phe Asp Ser Leu Leu Gly Val Asp Tyr Trp Tyr
                20                  25                  30

Gly Ile Pro Ser Ala Leu Arg Lys Asp Gly Ala Thr Val Tyr Val Thr
            35                  40                  45

Glu Val Ser Gln Leu Asp Thr Ser Glu Ala Arg Gly Glu Gln Leu Leu
        50                  55                  60

Thr Gln Val Glu Glu Ile Val Ala Ile Ser Gly Lys Pro Lys Val Asn
 65                  70                  75                  80

Leu Phe Gly His Ser His Gly Gly Pro Thr Ile Arg Tyr Val Ala Ala
                85                  90                  95

Val Arg Pro Asp Leu Val Ala Ser Val Thr Ser Ile Gly Ala Pro His
                100                 105                 110

Lys Gly Ser Ala Thr Ala Asp Phe Ile Arg Gln Val Pro Glu Gly Ser
            115                 120                 125

Ala Ser Glu Ala Ile Leu Ala Gly Ile Val Asn Gly Leu Gly Ala Leu
        130                 135                 140
```

-continued

```
Ile Asn Phe Leu Ser Gly Ser Ser Asp Thr Pro Gln Asn Ser Leu
145                 150                 155                 160

Gly Thr Leu Glu Ser Leu Asn Ser Glu Gly Ala Ala Arg Phe Asn Ala
            165                 170                 175

Arg Phe Pro Gln Gly Val Pro Thr Ser Ala Cys Gly Glu Gly Asp Tyr
            180                 185                 190

Val Val Asn Gly Val Arg Tyr Tyr Ser Trp Ser Gly Thr Ser Pro Leu
            195                 200                 205

Thr Asn Val Leu Asp Pro Ser Asp Leu Leu Gly Ala Thr Ser Leu
210                 215                 220

Thr Phe Gly Phe Glu Ala Asn Asp Gly Leu Val Gly Arg Cys Ser Ser
225                 230                 235                 240

Arg Leu Gly Met Val Ile Arg Asp Asn Tyr Arg Met Asn His Leu Asp
                245                 250                 255

Glu Val Asn Gln Thr Phe Gly Leu Thr Ser Ile Phe Glu Thr Ser Pro
            260                 265                 270

Val Ser Val Tyr Arg Gln Gln Ala Asn Arg Leu Lys Asn Ala Gly Leu
            275                 280                 285
```

<210> SEQ ID NO 2
<211> LENGTH: 864
<212> TYPE: DNA
<213> ORGANISM: Pseudomonas sp.

<400> SEQUENCE: 2

```
ttcggctcct cgaactacac caagacccag tacccgatcg tcctgaccca cggcatgctc      60
ggtttcgaca gcctgcttgg agtcgactac tggtacggca ttccctcagc cctgcgtaaa     120
gacggcgcca ccgtctacgt caccgaagtc agccagctcg acacctccga agcccgaggt     180
gagcaactgc tgacccaagt cgaggaaatc gtggccatca gcggcaagcc caaggtcaac     240
ctgttcggcc acagccatgg cgggcctacc atccgctacg ttgccgccgt cgcccggat      300
ctggtcgcct cggtcaccag cattggcgcg ccgcacaagg gttcggccac cgccgacttc     360
atccgccagg tgccggaagg atcggccagc gaagcgattc tggccgggat cgtcaatggt     420
ctgggtgcgc tgatcaactt cctttccggc agcagttcgg acaccccaca gaactcgctg     480
ggcacgctgg agtcactgaa ctccgaaggc gccgcacggt ttaacgcccg cttcccccag     540
ggggtaccaa ccagcgcctg cggcgagggc gattacgtgg tcaatggcgt cgcctattac     600
tcctggagcg gcaccacccc gctgaccaac gtactcgacc cctccgacct gctgctcggc     660
gccacctccc tgaccttcgg tttcgaggcc aacgatggtc tggtcggacg ctgcagctcc     720
cggctgggta tggtgatccg cgacaactac cggatgaacc acctggacga ggtgaaccag     780
accttcgggc tgaccagcat cttcgagacc agcccggtat cggtctatcg ccagcaagcc     840
aatcgcctga agaacgccgg gctc                                            864
```

<210> SEQ ID NO 3
<211> LENGTH: 335
<212> TYPE: PRT
<213> ORGANISM: Pseudomonas sp.

<400> SEQUENCE: 3

```
Met Lys Pro Leu Ile Tyr Leu Pro Leu Leu Gly Leu Gly Leu Leu
1               5                   10                  15

Gly Trp His Leu Ser Thr Pro Ala Pro Ser Pro Ser Ala Ser Pro
                20                  25                  30

Ala Pro Pro Gln Val Ser Ser Glu Lys Pro Ala Thr Ala His Met Asp
```

```
                    35                  40                  45
Leu Thr Arg Pro Val Ala Arg Ser Thr Asp Gln His Leu Pro Ala Ser
 50                  55                  60
Leu Arg Asp Thr Asp Val Asp Gly Gln Leu Glu Val Asp Ala Gln Gly
 65                  70                  75                  80
Asn Leu Val Ile Ser Asp Gln Leu Arg His Leu Phe Asp Tyr Phe Phe
                 85                  90                  95
Ser Thr Val Gly Glu Gln Ser Phe Glu Gln Ala Ser Thr Gly Ile Arg
                100                 105                 110
Asp Tyr Leu Ala Ser Gln Leu Arg Glu Pro Ala Leu Gly Gln Ala Leu
                115                 120                 125
Asp Leu Leu Asp Arg Tyr Ile Asn Tyr Lys Thr Glu Leu Val Glu Leu
            130                 135                 140
Glu Arg Arg Phe Pro Met Val Thr Glu Leu Asp Gly Leu Arg Ala Arg
145                 150                 155                 160
Glu Asp Ala Val Gln Arg Leu Arg Ala Ser Leu Phe Asn Ala Gln Glu
                165                 170                 175
His Ala Ala Phe Phe Ala Ser Glu Glu Val Tyr Asn Gln Phe Thr Leu
            180                 185                 190
Glu Arg Leu Ala Ile Leu His Asp Pro Ser Leu Asp Pro Gln Asp Lys
        195                 200                 205
Ala Glu Arg Ile Glu Arg Leu Arg Gly Leu Pro Asp Glu Leu Gln
210                 215                 220
Gln Leu Leu Val Pro Gln Leu His Leu Thr Leu Arg Gln Gln Thr Gln
225                 230                 235                 240
Gln Leu Leu Glu Gln Gly Ala Glu Pro Glu Gln Leu Arg Gln Leu Arg
                245                 250                 255
Leu Asn Leu Val Gly Pro Gln Ala Thr Glu Arg Leu Glu Ala Leu Asp
            260                 265                 270
Arg Gln Arg Ser Glu Trp Asp Gln Arg Leu Ser Gly Phe Asn Arg Glu
        275                 280                 285
Arg Gln Ala Ile Ile Ser Gln Pro Gly Leu Ala Asp Ser Asp Lys Gln
        290                 295                 300
Ala Ala Ile Glu Ala Leu Leu His Glu Gln Phe Ser Glu His Glu Arg
305                 310                 315                 320
Leu Arg Val Ser Ser Leu Leu Gly Leu Asp Ser Arg Ala Glu Arg
                325                 330                 335

<210> SEQ ID NO 4
<211> LENGTH: 1005
<212> TYPE: DNA
<213> ORGANISM: Pseudomonas sp.

<400> SEQUENCE: 4
atgaagccgc tgatttatct gcctttgctt cttggcctgg ggctgctcgg ctggcacctg      60
agcacgccgg cacccagccc atccagcgcc tcaccagcgc cgccacaagt cagcagtgaa     120
aaacctgcca cggctcacat ggacctgacc cgccccgtgg cccgcagcac cgaccagcat     180
ctgcccgcct cgctgcgcga taccgacgtc gatggccagc tggaggtcga cgcccagggc     240
aatctggtga tttccgacca gctgcgccac ctgttcgact atttcttcag caccgtcggc     300
gaacagtcgt tcgagcaggc cagcaccggt atccgcgact atctggccag ccagctgcgt     360
gaaccggctc tgggtcaggc cctggatctg ctggatcgct atatcaacta caagaccgag     420
ctggtggaac tggagcgacg cttcccgatg gtgaccgagc tggacggcct gcgtgcccgt     480
```

-continued

```
gaagatgccg tacagcgcct gcgcgccagc ctgttcaacg cgcaggagca cgccgccttc    540
ttcgccagcg aagaggtcta taaccagttc actcttgagc gtctggcgat actgcacgac    600
ccgtcgctgg atccgcagga caaggccgag cggatcgaac gtctgcgcga agggctaccc    660
gacgagttgc aacaattgct ggtaccgcaa ttacacctga ccctgcgcca gcagacccag    720
cagttgctgg agcaaggcgc cgagccgaac cagctacgcc aattgcgcct gaacctggtc    780
ggcccccagg caaccgaacg cctggaggca ctggaccgcc agcgcagcga atgggatcag    840
cgcctgagcg gcttcaatcg cgaacggcag gcgatcatca gccagccggg gctggccgac    900
agtgacaagc aggccgcgat tgaggccctg ctgcacgagc agttcagtga gcatgagcgg    960
ctgagggtca gcagtctgct gggactcgat agccgcgccg aacgc                   1005
```

```
<210> SEQ ID NO 5
<211> LENGTH: 26
<212> TYPE: PRT
<213> ORGANISM: Pseudomonas sp.

<400> SEQUENCE: 5

Phe Gly Ser Ser Asn Tyr Thr Lys Thr Gln Tyr Pro Ile Val Leu Thr
 1               5                  10                  15

His Gly Met Leu Gly Phe Asp Ser Leu Leu
            20                  25

<210> SEQ ID NO 6
<211> LENGTH: 20
<212> TYPE: DNA
<213> ORGANISM: Pseudomonas sp.
<220> FEATURE:
<223> OTHER INFORMATION: N= A or C or G or T/U or other

<400> SEQUENCE: 6
aactacacna agacncagta                                                 20

<210> SEQ ID NO 7
<211> LENGTH: 30
<212> TYPE: DNA
<213> ORGANISM: Artificial Sequence
<220> FEATURE:
<223> OTHER INFORMATION: Mutagen

<400> SEQUENCE: 7
ggggaattca ggactcgcat tatgcgcaac                                      30

<210> SEQ ID NO 8
<211> LENGTH: 30
<212> TYPE: DNA
<213> ORGANISM: Artificial Sequence
<220> FEATURE:
<223> OTHER INFORMATION: Mutagen

<400> SEQUENCE: 8
tttgaattca gagcccggcg ttcttcaggc                                      30

<210> SEQ ID NO 9
<211> LENGTH: 30
<212> TYPE: DNA
<213> ORGANISM: Pseudomonas sp.

<400> SEQUENCE: 9
tttgagctca gagcccggcg ttcttcaggc                                      30

<210> SEQ ID NO 10
```

```
<211> LENGTH: 30
<212> TYPE: DNA
<213> ORGANISM: Artificial Sequence
<220> FEATURE:
<223> OTHER INFORMATION: Mutagen

<400> SEQUENCE: 10
aaatctagat tcggctcctc gaactacacc                                    30

<210> SEQ ID NO 11
<211> LENGTH: 30
<212> TYPE: DNA
<213> ORGANISM: Artificial Sequence
<220> FEATURE:
<223> OTHER INFORMATION: Mutagen

<400> SEQUENCE: 11
ccctctagac tagcgttcgg cgcggctatc                                    30

<210> SEQ ID NO 12
<211> LENGTH: 30
<212> TYPE: DNA
<213> ORGANISM: Artificial Sequence
<220> FEATURE:
<223> OTHER INFORMATION: Mutagen

<400> SEQUENCE: 12
ccctctagat cagagcccgg cgttcttcag                                    30

<210> SEQ ID NO 13
<211> LENGTH: 30
<212> TYPE: DNA
<213> ORGANISM: Pseudomonas sp.

<400> SEQUENCE: 13
cccgaattca tacgaattaa agttgaaagc                                    30

<210> SEQ ID NO 14
<211> LENGTH: 30
<212> TYPE: DNA
<213> ORGANISM: Pseudomonas sp.

<400> SEQUENCE: 14
aaatctagag ttgaaaccaa ttaagtactc                                    30

<210> SEQ ID NO 15
<211> LENGTH: 30
<212> TYPE: DNA
<213> ORGANISM: Pseudomonas sp.

<400> SEQUENCE: 15
gggtctagat ccctaaggat gtactggatg                                    30

<210> SEQ ID NO 16
<211> LENGTH: 30
<212> TYPE: DNA
<213> ORGANISM: Pseudomonas sp.

<400> SEQUENCE: 16
tttaagctta gaaactcaac tgtcacagtg                                    30
```